United States Patent [19]

Cais et al.

[11] Patent Number: 4,510,058
[45] Date of Patent: Apr. 9, 1985

[54] METHOD FOR A NEW TYPE OF CHROMATOGRAPHY AND DEVICE THEREFOR

[75] Inventors: Michael Cais; Moshe Shimoni, both of Haifa, Israel

[73] Assignee: Technion Research & Development Foundation, Ltd., Technion, Israel

[21] Appl. No.: 518,811

[22] Filed: Jul. 29, 1983

[30] Foreign Application Priority Data

Aug. 15, 1982 [IL] Israel .................................. 66551

[51] Int. Cl.$^3$ .............................................. B01D 15/08
[52] U.S. Cl. .................................. 210/657; 210/198.2
[58] Field of Search ............ 210/635, 656, 657, 198.2; 55/67, 197, 386

[56] References Cited

U.S. PATENT DOCUMENTS

| | | | |
|---|---|---|---|
| 3,313,419 | 4/1967 | Schlitt ................................ | 210/656 |
| 3,483,986 | 12/1969 | Wright ................................ | 210/198.2 |
| 3,810,545 | 5/1974 | Filz et al. ........................... | 210/198.2 |
| 3,966,609 | 6/1976 | Godbille ............................. | 210/198.2 |
| 4,270,921 | 6/1981 | Graas .................................. | 210/656 |

Primary Examiner—John Adee
Attorney, Agent, or Firm—Schwartz, Jeffery, Schwaab, Mack, Blumenthal & Koch

[57] ABSTRACT

The present invention relates to a new type of chromatography technique, referred to as dynamic column chromatography, for separation of one or more compounds present in a solution, which is characterized by the existence of a moving solid adsorbent bed. According to the invention, the chromatographic system comprises a piston having at its bottom a sealing element and a longitudinal channel containing the adsorbent between two barriers and a test tube having at its bottom a multiple way valve. By pushing the piston into the test tube, the desired eluent which was prior forced through said valve is entering under intrinsic pressure of the closed system through the channel moving the adsorbed compounds to be separated between said barriers, the solution obtained going out through a nozzle located at one of the end parts of the piston. The dynamic column liquid chromatography is applicable to: silica gel chromatography, reversed phase liquid chromatography, affinity chromatography, capillary chromatography, chromato-focusing, gel filtration and ion exchange chromatography. In the dynamic column liquid chromatography, the equilibrium distribution of the compounds between the adsorbent and liquid is established very rapidly, resulting in sharp and narrow zones of the separated fractions.

26 Claims, 14 Drawing Figures

Fig. II

METHOD FOR A NEW TYPE OF CHROMATOGRAPHY AND DEVICE THEREFOR

BACKGROUND OF THE INVENTION

The present invention relates to a new method of chromatography hereafter referred to as Dynamic column Liquid Chromatography (DCLC) for separating two or more components. More particularly the invention relates to a new method for separation of two or more compounds present in a solution using a moving bed chromatographic system.

Chromatography is a term that describes a number of physical methods used in chemistry and biology to separate and identify mixtures of chemical compounds. The principle behind all chromatography variants lies in the repeated subjection of a mixture of chemical compounds to extraction by liquid or adsorption on a solid surface. The mixture is moved physically over a stationary phase (bed or column), which may be either a solid or a liquid immobilized in the pores of a solid (located in said bed or column). The separation of chemical compounds by chromatography may make use of one or more of the following physico-chemical forces, depending upon the particular chromatographic system:
(a) Differences in adsorption to the porous medium, the so called sorbent.
(b) Differences between the relative solubilities of a liquid coating the inert medium (stationary phase) and the liquid, called mobile phase, percolating through the porous column.
(c) Differences in ion exchange with the sorbent.
(d) Differences in molecular size as the solution percolates through a gel of very small size.

Chromatography is also named preparative chromatography when it is used for isolation of a fraction from a mixture for further uses such as spectroscopy, identification, synthesis for research or commercial purposes.

The original work on chromatography is based on differences in adsorption over an inert material packed in a column. The separation of components, known also as partition chromatography is based on the relative solubilities in the solvent which is passed over the column. The resolution obtained in this chromatography depends upon the pH and ionic strength of the solvent—the mobile phase—and the relative solubilities of the constituents in the two phases; the various materials may be eluted with an appropriate solvent and the liquid fractions collected in a series of tubes and subsequently analysed by chemical or physical methods. Thin layer chromatography (TLC) and paper chromatography, are based on differences between the relative adsorption of a component onto an inert medium. In TLC, the stationary phase consists of a thin layer of a finely divided substance applied to a sheet or plastic backing or to a glass plate. Sorbents commonly used, and commercially available as finished plates, include alumina, silica gel and cellulose. In paper chromatography, the mobile phase may move upwards by capillary action, so called ascending chromatography, or downwards by gravity, so called descending chromatography.

Ion exchange chromatography, involves the separation of molecules based on their ionic charge. The sorbent or stationary phase, consists of polymers with covalently bound ions. In cation exchange resins, the tightly bound ions are negatively charged and are associated with positive ions that are loosely attached by electrostatic charges. The positively charged substances to be separated from a mixture are first adsorbed to the sorbent, displacing the cations present in the resin. The solution is buffered at a pH that will facilitate the binding and then eluted with the same buffer to remove the non-binding fractions of the solution. An anion exchanger operates in exactly the same way, except that its covalently bound ions are oppositively charged to attract the anions from the solution.

The separation based on differences in molecular size is encountered in gel filtration, also known as molecular sieve chromatography. This method separates molecules according to their size, although the shape of the molecule affects the filtration to some extent. The gels are in the form of beads containing a network of openings of pores in which small molecules may be entrapped. The vast commercial interest in chromatography in general and preparative liquid chromatography in particular, is manifested by the large number of publications suggesting various microparticulate column packings and prepacked columns claiming to obtain better separation than the known adsorbents used in this field.

SUMMARY OF THE INVENTION

The present invention embodies a new concept for chromatography in which known adsorbents are utilized, but the separation is very fast and more easily conducted. The new concept of the chromatography according to the present invention, is to utilize a dynamic column in which the bed with the adsorbent is moving in contrast to the conventional chromatography technique wherein the adsorbent material is stationary.

DETAILED DESCRIPTION OF PREFERRED EMBODIMENTS

Thus the invention relates to a method for a new type of chromatography technique hereafter referred to as dynamic column liquid chromatography (DCLC) for separation of one or more compounds present in a solution characterized by the existence of a moving solid adsorbent bed, which comprises a piston having at its bottom a sealing element and a longitudinal channel containing an adsorbent held between two barriers, a test tube having at its bottom a multiple way valve, said piston snugly fitting into the test tube, wherein by pushing the piston into the test tube, the desired eluent which was prior forced through said valve is entering through the channel moving the adsorbed compounds to be separated between said barriers; the solution obtained going out through a nozzle located at one of the end parts of the piston. The general case which seems to be more frequently encountered is the use of a solid adsorbent column or bed, as adsorbent zone, in which case the method will compete most favourably with the conventional chromatography techniques. The method is very accurate and has the following main advantages over the conventional chromatography:
(a) In contrast to the gravitational flow which exists in the conventional chromatography, in the dynamic column liquid chromatography some pressure is inherently exerted in the adsorbent bed, which imparts a better resolution in the separation of the constituents.

(b) The method is very rapid, also as a result of the intrinsic pressure exerted in the system.

(c) The method requires less eluent than in the conventional chromatography.

(d) The presence of intrinsic pressure in the dynamic chromatography system enables to utilize an adsorbent with smaller particles size than in the conventional chromatography, which enables a higher sensitivity.

The multiple way valve is very important when several consecutive eluents have to be introduced in the test tube, being further passed through the adsorbent bed thus obtaining the desired fractionation. When the adsorbent bed is utilized mainly for pretreatment of a sample, or for removing of one compound, the valve requirement is not mandatory and a simple test tube closed at the bottom, fitted to the piston may be utilized. In this case the eluent should be introduced into the test tube prior to pushing down the piston. Of course even when no fractionation is required, it seems that the test tube with a valve will be more advantageous to be utilized, concerning washing the adsorbent and introduction of the eluent by its aspiration through the valve.

The sealing element slides along the inner walls of the test tube, at the same time staying in good contact with said inner walls permitting a snugly fitting of the piston into the test tube. The sealing element will generally consist of a rubber or other suitable material O-ring having an orifice bore and adapted to slide along the inner walls of the test tube. When the device will be made of glass, the polish on the outer wall of the piston may be accordingly manufactured so that it could replace the O-ring.

The entire method is very flexible and could be applied in a large number of applications with various embodiments, and will be therefore included in the concept of the present invention. A problem which exists in all kinds of chromatography, is an even application of the sample to the surface of the bed. When the sample is applied directly by gravitational flow, an even application may be relatively difficult, as the bed has a tendency to whirl up when the sample is introduced. For this reason it is particularly important to have the surface protected such as a piece of rayon filter paper. One manufacturer of columns (Pharmacia Fine Chemicals AB) equips some of the columns with a special device called sample applicator, that serves to protect the bed surface. In this device, a thin nylon fabric is mounted at the end of a short piece of perspex tubing fitting inside the chromatographic tube. Such device increases of course the costs of the equipment in addition to the disadvantage that its presence causes pressure to the flow of the sample slowing down its perculation through the column. In most of the chromatography systems utilizing the present invention, the problem of an even application is much alleviated. In the dynamic flow which exists in the chromatographic bed, the liquid being forced upwards upon pushing the piston into the test tube, no whirl tendency will exist due to sample introduction. Moreover, the pressure exerted in the system from pushing the piston into the test tube, will accelerate the flow of the sample. Another approach to assist an even application of the sample, is to incorporate above the bed another suitable adsorbent different from the adsorbent already present in the bed, having the role of preconcentrating the sample and thus assisting to get a narrow band of resolution. A typical example of such a suitable adsorbent is rough silica, which differs from the active silica with its high adsorbent properties.

The particle size and the particle size distribution must be carefully controlled in most of the conventional chromatography operations. As known, a bed consisting of small particles will generally give good resolution. The reason is that the mechanisms that give rise to zone broadening are amplified, as the particle size is increased. With large particles, diffusion in and out of the particles takes longer. The flow pattern in a bed of large particles is inferior, giving rise to more remixing. On the other hand, the resistance to flow in a bed packed with large particles is lower and the maximum flow rate that can be attained is higher. Thus in the conventional chromatography operations a compromise with respect to particle size should be reached, giving maximum zone resolution under the flow conditions required. In the new DCLC method according to the present invention, small particle size of adsorbent can be utilized without incurring the disadvantage encountered in the known methods, the small pressure inherently exerted in the system does overcome the resistance to flow raised by the small particle size of the particles. Thus this method can be utilized even for critical fractionation purposes when the use of a finer grade material will be mandatory in order to obtain the desired resolution.

In one of our prior patent applications (Ger. Offen. No. 3126926.5) a new method of mass transport and separation through selective barriers was disclosed using a device having similar components as in the present invention. As mentioned therein, the device consists of a mixer-separator which possesses a membrane and a mixing reservoir into which said mixer-separator is pushed. On the mixer-separator there are means for accumulating of an air pocket to decrease the pressure exerted on the membrane. During operation of the mixer-separator, a determined amount of air is entrapped in the air pocket, which upon compression acts as a cushion or shock absorber to take up part of the pressure resulting from the membrane resistance to the liquid flow. For the dynamic column liquid chromatography according to the present invention, the air pocket requirement might be considered less mandatory than in the previous case. However for certain systems wherein relative high pressures will be involved, the air pocket seems to have an important role, the entrapped amount of air forcing back into the test tube any liquid which may have creeped up in the space between the inner walls of the test tube and the outer walls of the terminal end of the piston. The amount of air entrapped by said means on the piston will depend on many factors such as the type of barrier, constituents of the mixtures to be separated and the particular conditions exerting in the specific chromatographic system. A particular advantage to such an air pocket is realized in the case in which complete avoidance of eluent leakage is effected with an O-ring, located at the bottom of the piston, having the role of sealing element.

The method according to the present invention can be successfully utilized in the various areas of chromatography: silica gel chromatography, reversed phase liquid chromatography, capillary chromatography, affinity chromatography, chromatofocusing, size-exclusion chromatography (also known under the name gel filtration) and ion exchange chromatography.

Silica gel chromatography, is one of the most common chromatography methods. Silica gel being by far one of the best known adsorbent being relatively inexpensive compared with other materials. The separation results obtained with silica gel in the method according to the present invention, are substantially the same or better concerning accuracy of separation and recovery yields to those obtained in the conventional techniques, but is more convenient by being faster and requiring also less solvent. It also has a particular advantage that the column can be re-usable. In addition smaller size silica gel particles and denser packing can be used with the resulting advantages of higher separation.

Reversed phase liquid chromatography is characterized by the fact that its stationary phase is less polar than the mobile phase. The main drawback with silica gel is that only a partial recovery of the compounds passing through such a bed could be recovered. In view of the advantages of the DCLC according to the present invention, the reversed phase liquid chromatography could be also successfully utilized in preparative chromatography. Recently, capillary chromatography received more interest particularly in view of developments in microcolumns for high performance liquid chromatography. The reason for these developments lies in the following advantages of this type of chromatography:

(a) Potential achievement of greater separation efficiencies for complex mixtures and hard to resolve solutes.
(b) A substantial decrease in consumption of eluent.

The DCLC method according to the present invention could easily be applied for capillary chromatography providing a narrow channel in the piston previously described.

Gel filtration, also known as size-exclusion chromatography is receiving more and more interest in the purification of biological substances using an adequate adsorbent as separation media. Good results were obtained in the separation of labelled Iodine-hCG from labelled Iodine using a Sephadex G-type (produced by Pharmacia Fine Chemicals, Sweden) adsorbent, using the dynamic chromatography according to the present invention, (See Example 3). Gel filtration chromatography is also considered as a simple and rapid method for desalting or change of buffer. The gel bed should be equilbrated before the experiment with a solution with the ionic composition that is desired, for example distilled water is case of desalting. The elution is performed with the same liquid. In view of the high rates which may be involved, the whole operation may be completed in a short period of time collecting the desalted material in a few minutes. Other areas for gel filtration chromatography envisaged with the dynamic chromatography will be pretreatment before HPLC and concentration of diluted samples followed by separation.

Chromato-focusing is largely used for separating proteins according to their isolectric points. Since chromato-focusing produces extremely narrow bands of separated material, and requires generally long narrow columns, it appears that the dynamic column liquid chromatography will be ideal for this type of chromatography, providing a narrow piston for the device described before.

The DCLC is also convenient for ion exchange chromatography, well known as one of the most popular separation techniques. Several experiments were performed for separating copper sulfate and sodium bichromate on Dowex 50 WX 8, as adsorbent. (See Example 2). It was found that substantial advantages in term of time, solvent volume and convenience could be achieved by using the DCLC.

Another advantage of the DCLC according to the present invention, is a substantial decrease of the dead volume. As known dead volume is defined as the volume of the liquid in the interstitial space between the grains of the adsorbent in the bed. In most of the conventional chromatography operations, the dead volume constitutes a problem which affects the determination of an accurate result. In the DCLC, because dense packing is possible, the equilibrium distribution of the substance between the adsorbent and liquid is established very rapidly with very low dead volume. Accordingly, it will be possible to obtain sharp and narrow zones. This is very important in fractionations experiments wherein the differences in elution volume between the substances is generally small. In particular for gel filtration large dead volumes will impair the resolution obtained.

According to another embodiment, the adsorbent is present into a cartridge which is inserted into the longitudinal channel of the piston. In this manner, the chromatography device will be ready for use for many purposes only by replacing the cartridge by one containing the suitable adsorbent. FIG. 5 attached to the specification illustrates this embodiment. The method is very simple and its versatility could be mentioned among its various advantages. There are many embodiments which can be envisaged for the device utilizing the method according to the present invention. Some of these embodiments are presented hereafter with the attached FIGS. 1 to 9, being understood that these are given only for a better understanding of the invention without being limited thereto.

In FIG. 1a, the test tube (1) is equipped with a Luer lock (2) to which a three way valve (3) is attached. The desired eluent (E) is forced into the test tube (1). The piston (5) has a longitudinal channel into which the adsorbent (6) is located being held by the two membranes (7,8) at the top and bottom of the piston. Above the upper membrane (8) there is a stopper (9) provided with a nozzle (10) through which the separated fraction from the adsorbent bed is collected. At the lower part of the piston there is an O-ring (17), which has the role of sealing, being adapted to slide along the inner walls of the test tube (1).

In FIG. 1b, which shows in enlargement a variation of the embodiment depicted in FIG. 1a below the plane defined by A—A', a groove (12) is provided in the piston (5) as means for accumulating a gas pocket. The groove in the piston may be horizontal, vertical or spiral.

In FIG. 2, no valve exists at the bottom of the test tube (14), a limited amount of the chosen eluent (15) being introduced from the beginning in the test tube (14). The piston (16) possesses the longitudinal channel in which the adsorbent (17) is located held by the two membranes (19,20). Above the upper membrane (20) there is a stopper (21). The nozzle (22) through which the separated fraction from the adsorbent bed is collected, is connected to the piston (16). At the lower part there is the O-ring (18) as a sealing element. This device could be utilized when no fractionation is required, the operation consisting of only one cycle with a single eluent.

In FIG. 3, the test tube (23) is exactly as in FIG. 2, without a valve at its bottom. The piston (24) possesses the longitudinal channel into which the adsorbent (26) is located being held by the two membranes (26,27). Above the upper membrane (27) there is a stopper (28) provided, with a nozzle (29) through which the separated fraction from the adsorbent bed is collected. At the bottom of the piston there is the O-ring (31) as a sealing element.

In FIG. 4, there is shown the simplest form of the device also without a valve at the bottom of the test tube and stopper at the top of the piston. A limited amount of the chosen eluent (32) is introduced from the beginning in the test tube (33). The piston (34) has a longitudinal channel in which the adsorbent (35) is present being held between the two barriers—membranes or filters—(36,37). The O-ring (38) is located at the lower part of the piston and has the role of sealing and being adapted to slide along the inner walls of the test tube (33). Connected to the channel with the adsorbent (35) there is a nozzle (39) through which the separated fraction is collected.

In FIG. 5, the method is illustrated wherein a cartridge (40) containing the desired adsorbent (41) is introduced into the longitudinal channel (42) of the piston (43). The collection of the 44 can be done through a nozzle as described in the previous Figures. The O-ring sealing (45) is present at the lower part of the piston (43). The mode of operation is very simple as will be hereafter described in conjunction with FIG. 1a. The piston (43) is pushed down in the test tube (46) which is filled with the chosen eluent (44). This will cause the eluent to be forced through lower membrane ($F_1$), not shown in FIG. 5 then through the adsorbent (41) present in the longitudinal channel of the piston (43), thereafter through an upper membrane (47) and finally through a nozzle (as shown, e.g. in FIG. 4). When filled with a suitable support material (41) it will act as a chromatography column. Refilling of the test tube (46) is effected simply by unlocking the test tube outlet and forcing more eluent through a valve (as shown in, e.g., FIG. 1).

In the remaining figures, various elements of the depicted embodiments are designated as in FIGS. 1a and 6, respectively, unless otherwise indicated.

In FIG. 6, there is shown an embodiment of the dynamic column in which the column piston (48) moves upwards into the test tube (49) so that the eluent passes through first and second upper membranes (50,51) and finally exits through through a vertical narrow channel (52) in direct continuation of the column chromatographic support material. FIG. 7 is a modification of the dynamic column of FIG. 6, whereby a column solvent reservoir is connected (53) to the dynamic column.

Figure 1A:
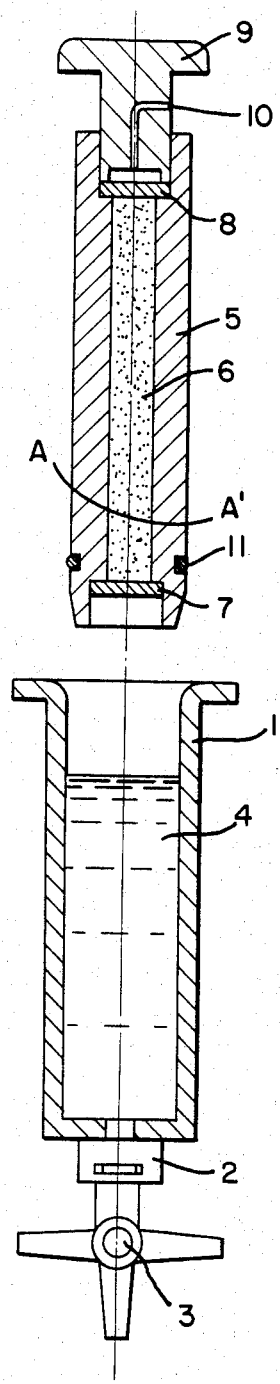
Figure 1B:
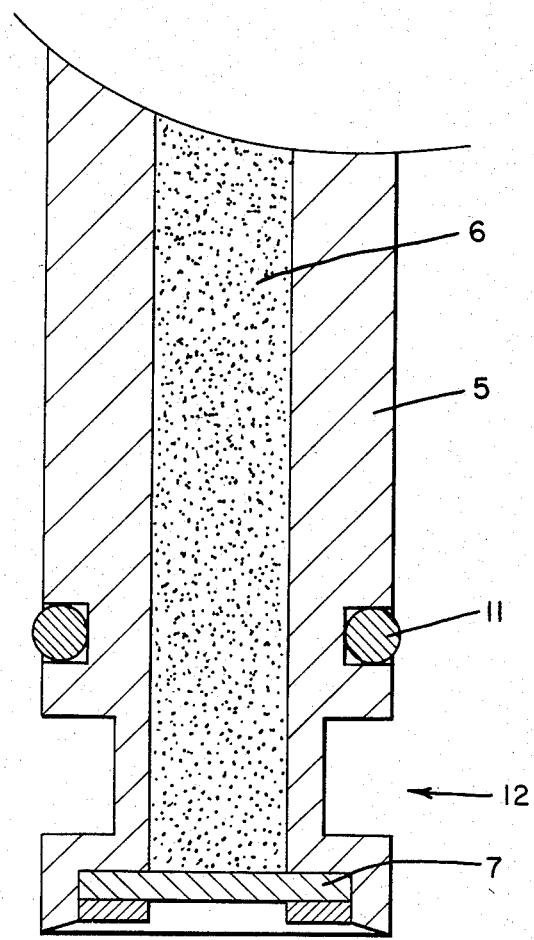
Figure 2:
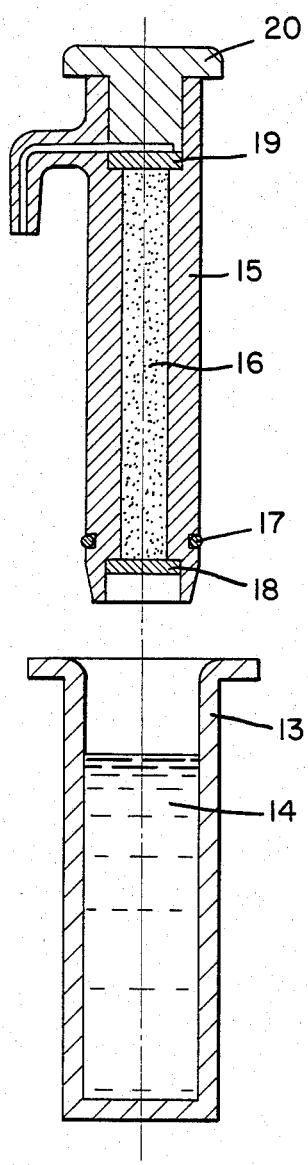
Figure 3:
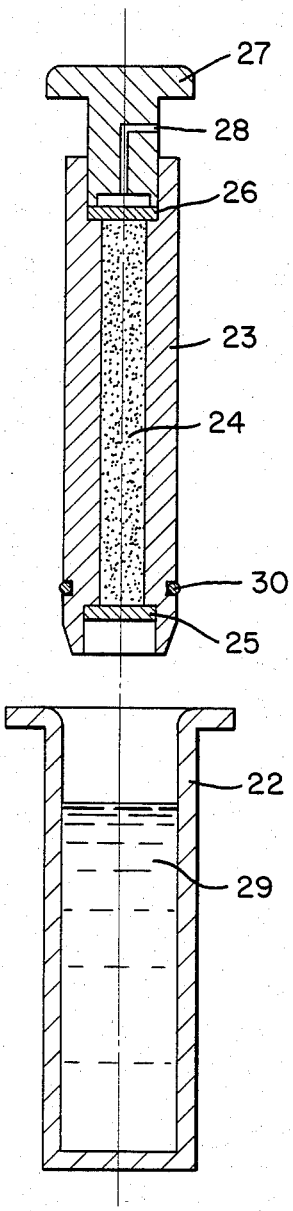
Figure 4:
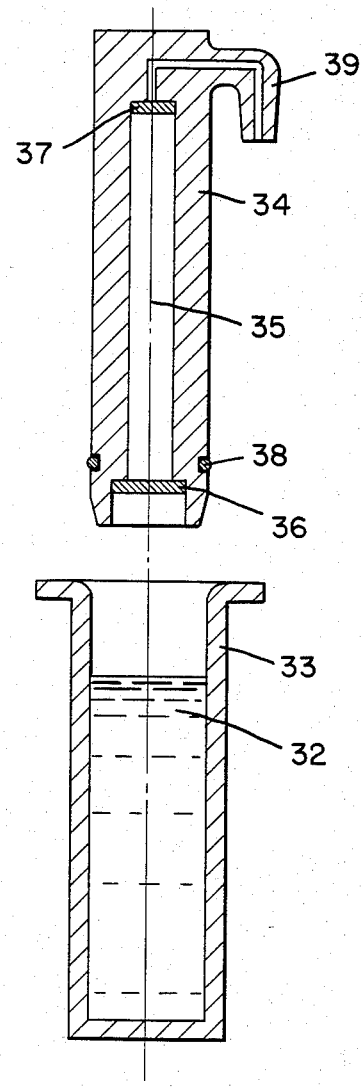
Figure 5:
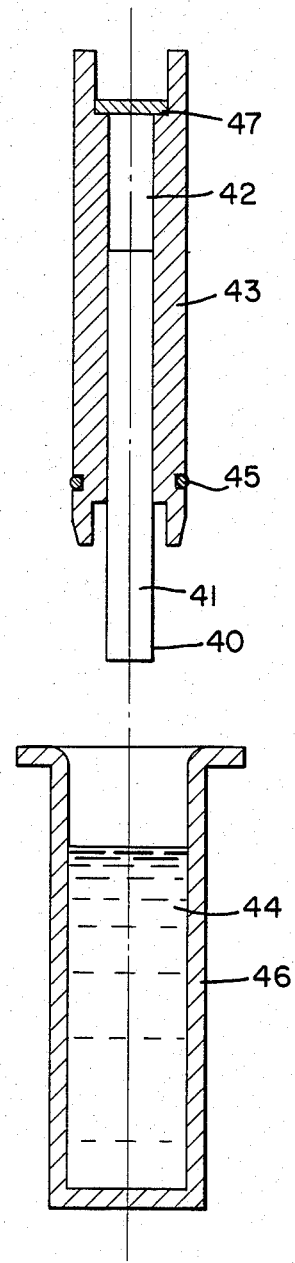
Figure 6:
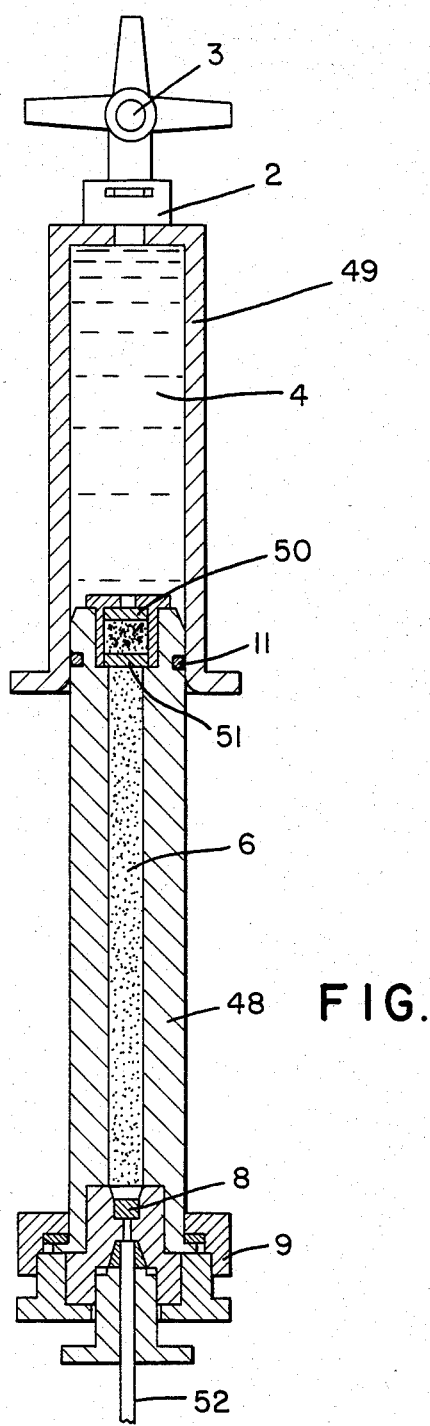
Figure 7:
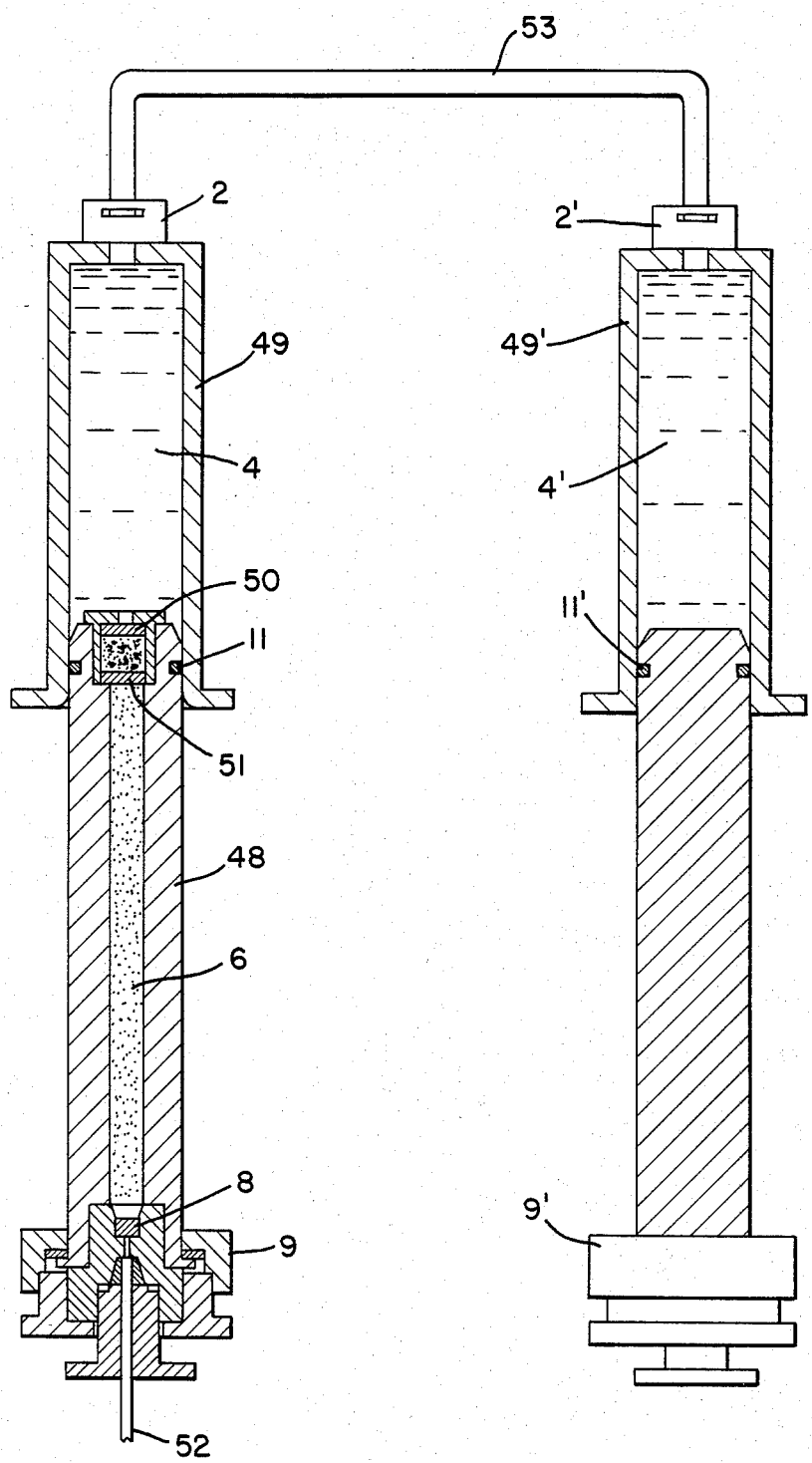
Figure 8:
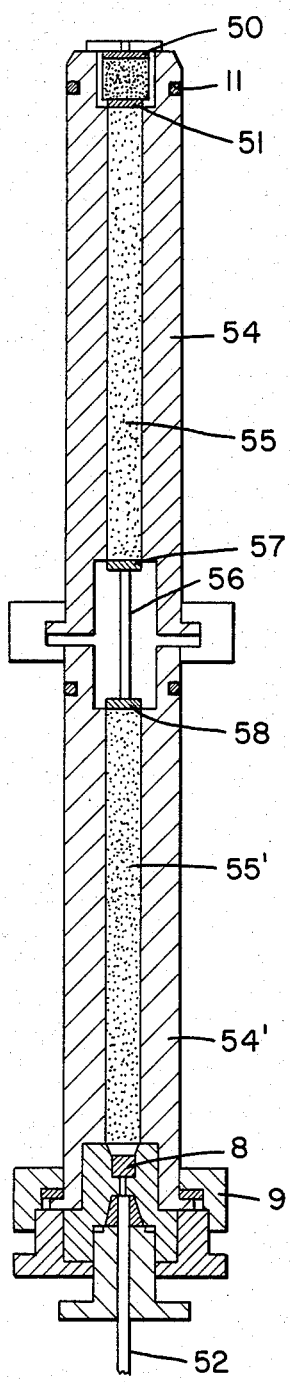
FIG. 8 illustrates an embodiment which shows the piston of the dynamic columns consisting of two or more subunits, (54,54) each one containing the same or different adsorbents (55,55'), connected by a tube (56) having membranes (57,58) at its inlet and outlet, respectively, with the possibility of collecting the eluent resulting from each subunit.
Figure 9:
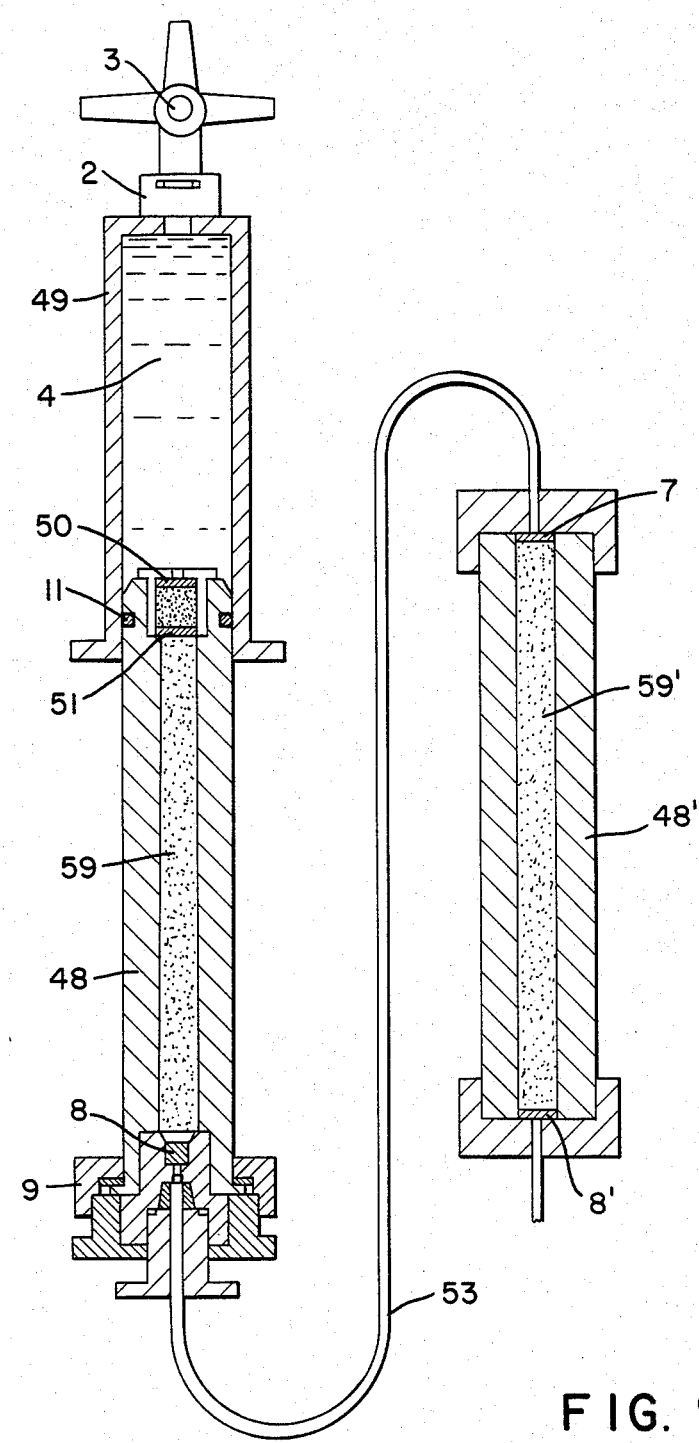
FIG. 9 illustrates another embodiment which shows the versatility of the DCLC whereby the utility can be further extended; according to this embodiment, the exiting eluent is conveyed to another column which contains the same or different adsorbent (59,59).

In principle the dynamic chromatography can be envisaged to be utilized also in liquid ion exchangers. Liquid ion exchangers are defined as liquid-liquid extraction systems that operate, at least formally, by interchange of ions at the interface between an aqueous solution and an immiscible solvent with negligible distribution of the extractant to the aqueous phase. Liquid anion-exchangers are used in reversed-phase extraction chromatography. In this technique, the support material (silica gel, cellulose powder etc.) impregnated with the liquid anion-exchanger, is used as the stationary phase and an aqueous solution of an acid or one of its salts is used as the eluent (mobil phase). For the present invention, the membrane should be so selected to be permeable only for the eluent but not for the liquid ion exchanger which should remain in the longitudinal channel of the piston.

The device to be utilized in the DCLC according to the present invention can be made from any inert material such as glass, polyethylene or any other suitable plastic material and even metal could be considered for some special uses.

The invention will now be further illustrated by the following Examples without being limited thereto or to the embodiments described in the specification. On the contrary it is intended to cover all alternatives, modifications and equivalents as may be included within the scope of the invention as defined by the appended Claims.

EXAMPLE 1

Separation of a mixture of Ferocene and Ferocene Aldehyde (a) Packing Method 1.0 g of silica (Merk, Kieselgel H, Type 60) is dispersed in 5 ml of a degassed solution of dichloromethane/hexane 1:1 in the locked test tube to make a slurry. The piston equipped with the stopper and the upper membrane is inserted into the test tube until firm contact between 'O'-ring and the test tube is reached.

The whole unit is inverted standing vertically on the stopper and the air is removed through the outlet in the test tube. The test tube outlet is then locked and packing is effected by moving the test tube down the stationary piston at a flow rate of about 1 ml/min. When the silica bed is completely settled the test tube outlet is unlocked and the test tube removed from the piston. The lower membrane is installed and the column is ready for sample application.

(b) Sample Application

A mixture of Ferocene and Ferocene aldehyde is dissolved in 0.2–0.4 ml of dichloromethane and the solution is applied onto the lower membrane of the vertically standing column. The solution penetrates the membrane and the components are adsorbed on silica. This process could be accelerated by applying some air pressure using the locked test tube.

(c) Elution

The packed piston is inserted into the test tube containing 5 ml of the chosen eluent. Air is removed as during packing of the column and elution is effected by the descent of the piston into the filled test tube at a flow rate of about 1 ml/min.

TABLE I

| Fr. No. | Eluent Volume | Eluent | Weight of Residue | Characterisation |
|---|---|---|---|---|
| (I) Separation of a Model Mixture Containing Ferocene (13 mg.) and Ferocene Aldehyde (19 mg.) | | | | |
| 0 | 1 ml | Hexane | 0 | Blank |
| 1 | " | " | 11.4 mg | Ferocene |
| 2 | " | " | 0.79 | Ferocene |
| 3 | " | " | 0.31 | Ferocene |
| 4 | " | Dichloromethane | Traces | Blank |
| 5 | " | " | 1.79 | Aldehyde |
| 6 | " | " | 13.36 | Aldehyde |
| 7 | " | " | 4.59 | Aldehyde |
| 8 | " | " | 1.69 | Aldehyde |
| 9 | " | " | Traces | Blank |
| (II) Separation of a Model Mixture Containing Ferocene (25.3 mg) and Ferocene Aldehyde (15.6 mg) | | | | |
| 0 | 1 ml | Hexane | 0.2 mg | Ferocene |
| 1 | " | " | 19.0 mg | Ferocene |
| 2 | " | " | 1.7 mg | Ferocene |
| 3 | " | " | 0.3 mg | Ferocene |
| 4 | " | " | 0 | Blank |
| 5 | " | Dichloromethane | 0 | Blank |
| 6 | " | " | 0.2 mg | Aldehyde |
| 7 | " | " | 11.5 mg | Aldehyde |
| 8 | " | " | 2.9 mg | Aldehyde |
| 9 | " | " | 0.7 mg | Aldehyde |
| 10 | " | " | 0 | Blank |

EXAMPLE 6

Separation of $Na_2Cr_2O_7.2H_2O$ from $CuSO_4 5H_2O$ by ion exchange

The adsorbent consisted of DOWEX 50 WX8 (200–400 mesh size). The adsorbent was first washed and after left for about 30 minutes in distilled water acidified with hydrochloric acid (2N). The acidity was subsequently removed by washing with distilled water and the neutral adsorbent introduced into the channel of the piston. The two membranes which held the adsorbent bed consisted of two discs of porous polyethylene filter.

The aqueous solution sample consisted of 359.3 mg of $Na_2Cr_2O_7.2H_2O$ and 369.7 mg $CuSO_4.5H_2O$ dissolved in 1 cc of water. The sample was introduced through the adsorbent, the amount of sample taken for analysis being 100 μl. The ions were washed from the column and separated as follows:
- the anions by distilled water;
- the cations by an acidic solution consisting of 2N hydrochloric acid.

The portions were collected in test tubes. The end of washing was determined according to the colour of the exit solution. The samples were further quantitatively analysed by drying the various portions at 110° C. and weighing the dry residue. A blank experiment for the residue was performed wherein 100 μl of the sample were introduced in a test tube and dried at 110° C. The solid residue weighed 68.5 mg.

The results of the various dried fractions weighed are given in the following Table 2. In Expt. 2, the column after Expt. 1 was washed to neutral and neutralized.

TABLE 2

Separation by ion exchange with the dynamic chromatography

| Expt. No. | No. of the fraction | The eluent utilized | The weight of the dried fraction (mg) | Total weight (mg) | Remarks |
|---|---|---|---|---|---|
| 1 | 1 | $H_2O$ | 43.0 | | |
| | 2 | " | 0.2 | | |
| | 3 | " | 0 | 43.2 | * |
| | 4 | HCl(2N) | 0.5 | | |
| | 5 | " | 15.2 | | |
| | 6 | " | 27.5 | | |
| | 7 | " | 3.2 | | |
| | 8 | " | 1.3 | 47.7 | * |
| 2 | 1 | $H_2O$ | 44.2 | | |
| | 2 | " | 1.1 | | |
| | 3 | " | 0.1 | 45.3 | * |
| | 4 | HCl(2N) | 0.4 | | |
| | 5 | " | 2.3 | | |
| | 6 | " | 34.0 | | |
| | 7 | " | 5.7 | | |
| | 8 | " | 0.8 | 43.2 | * |

*Fraction without colour.

From the above results it appears that after 8 fractions percolated through the adsorbent, substantially all the compounds were removed and separated.

In order to point out the efficiency of the DCLC according to the present invention, a comparative test was performed using conventional chromatography, by gravitational flow, with the same amount of 100 μl of sample and the same adsorbent. The results are presented in the following Table 3:

TABLE 3

Separation by ion exchange using a conventional chromatography column:

| No. of fraction | The eluent utilized | The weight of the dried fraction (mg) | Total weight (mg) | Remarks |
|---|---|---|---|---|
| 1 | $H_2O$ | 0.8 | | |
| 2 | " | 50.3 | | |
| 3 | " | 1.3 | | |
| 4 | " | 0.5 | | |
| 5 | " | 0.2 | | |
| 6 | " | 0.3 | | |
| 7 | " | 0.4 | | |
| 8 | " | 0.1 | | |
| 9 | " | 0.3 | | |
| 10 | " | 0.4 | | |
| 11 | " | 0.1 | | |
| 12 | " | 0.3 | | |
| 13 | " | 0.1 | 54.9 | Fraction without colour |
| 14 | HCl(2N) | 0.0 | | |
| 15 | " | 2.3 | | |
| 16 | " | 23.0 | | |
| 17 | " | 12.7 | | |
| 18 | " | 3.3 | | |
| 19 | " | 1.4 | | |
| 20 | " | 1.4 | 44.1 | Fraction without colour |

EXAMPLE 3

In this experiment a solution of 100 μl of β-hCG containing 30–35% labelled iodine (*$I_2$) was separated by the DCLC using a Sephadex G-10 adsorbent. The elution was performed with 10 ml of buffer at pH of about 8. Each fraction consisted of about 0.4 ml.

The results are presented in the following Table 4:

TABLE 4

Separation of β - h CG containing *I$_2$ on Sephadex G-10, eluted with a buffer (pH about 8)

| Fraction No. | Blank | cpm determined | Total |
|---|---|---|---|
| | 29.0 | 0 | |
| 2 | 9348.0 | 9578.0 | |
| 3 | 1946.0 | 1962.8 | |
| 4 | 292.0 | 267.7 | |
| 5 | 130.0 | 104.8 | |
| 6 | 114.0 | 84.5 | |
| 7 | 108.0 | 82.0 | |
| 8 | 78.0 | 48.2 | 12125 cpm |
| 9 | 79.0 | 49.6 | |
| 10 | 98.0 | 67.7 | |
| 11 | 134.0 | 102.9 | |
| 12 | 182.0 | 152.5 | |
| 13 | 414.0 | 389.3 | |
| 14 | 485.0 | 464.4 | |
| 15 | 766.0 | 757.5 | |
| 16 | 854.0 | 834.7 | |
| 17 | 635.0 | 615.5 | |
| 18 | 450.0 | 424.6 | |
| 19 | 504.0 | 486.4 | |
| 20 | 378.0 | 348.5 | |
| 21 | 284.0 | 256.8 | |
| 22 | 158.0 | 127.7 | |
| 23 | 131.0 | 99.8 | 5169 cpm |
| Total | 20534.0 | 20594.4 | 17294 |

It appears that the recovery is about 85%. This separation when performed in a conventional chromatography will require much more eluent and will take also more time for separation.

EXAMPLE 4

In this experiment a solution of dyestuff mixture consisting of: 35% Ceres red 7B; 28% Nitro fast blue 2B; 25% Nitro fast violet FBL and 12% Ceres yellow R (all being volume percentages) was separated with the DCLC method. This dyestuff mixture was provided by Merck (catalogue Number 9354).

An amount of 30 μl of the dyestuff mixture in dichloromethane was injected in a DCLC containing LICHROPREP Si-60 (Trade Mark produced by Merck, cat. No. 9336), a silica-based adsorbent having particle size of 15–25 μm Silica. The column sizes were as follows: length 10.6 cm and internal diameter 10 mm. The flow rate was 2 ml/min and the eluant was dichloromethane.

Figure 10:
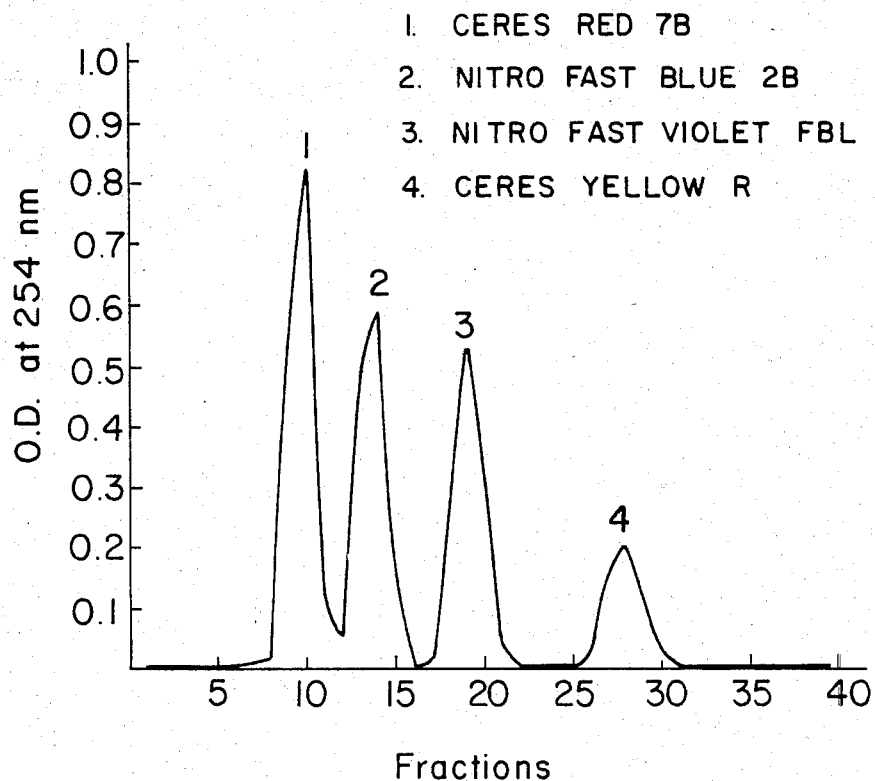
FIGS. 10 to 12 represent in a graphic form the results of the separation for various mixtures as described in Examples 4, 5 and 6.

The results of the separation are presented in FIG. 10 in the form of graphs, optical density (O.D.) at 254 nm versus the fractions. As appears from the graphs a fast and clean separation was received.

EXAMPLE 5

In this experiment a mixture of polycyclic aromatics consisting of: 50% benzene; 30% naphthalene and 20% anthracene (volume percentages) in n-heptane solution was separated with the DCLC method.

The sample injected consisted of 50 μl using a column with the same sizes as in Example 4 containing the same adsorbent. The flow rate was 2 ml/min, the volume of each fraction being 1 ml. The eluant was n-heptane.

Figure 11:
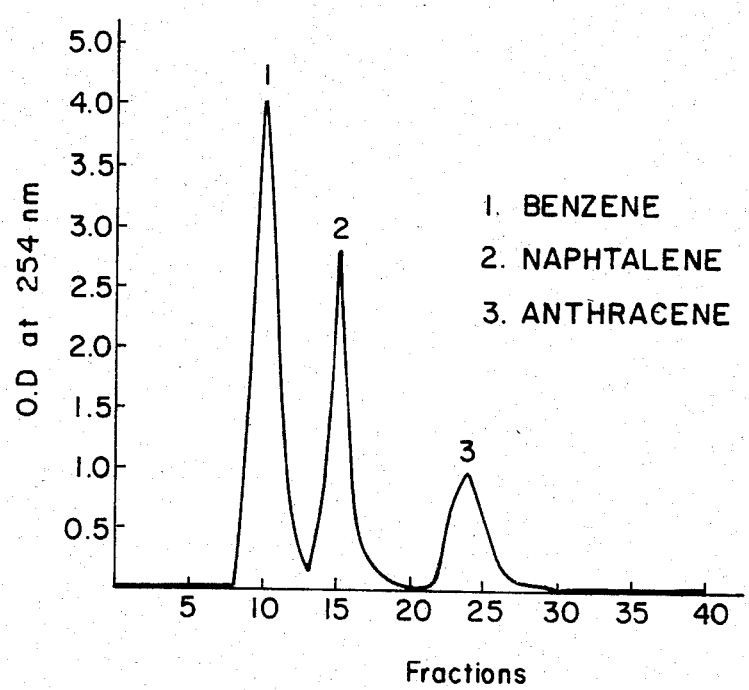

The results of the separation are presented in FIG. 11 in the form of graphs, optical density (O.D.) at 254 nm versus the fractions. As appears from said graphs, the components were separated into three sharp peaks.

EXAMPLE 6

In this experiment a mixture of alkyl phthalates was separated with the DCLC method using a column as in Example 4 with the same adsorbent.

Figure 12:
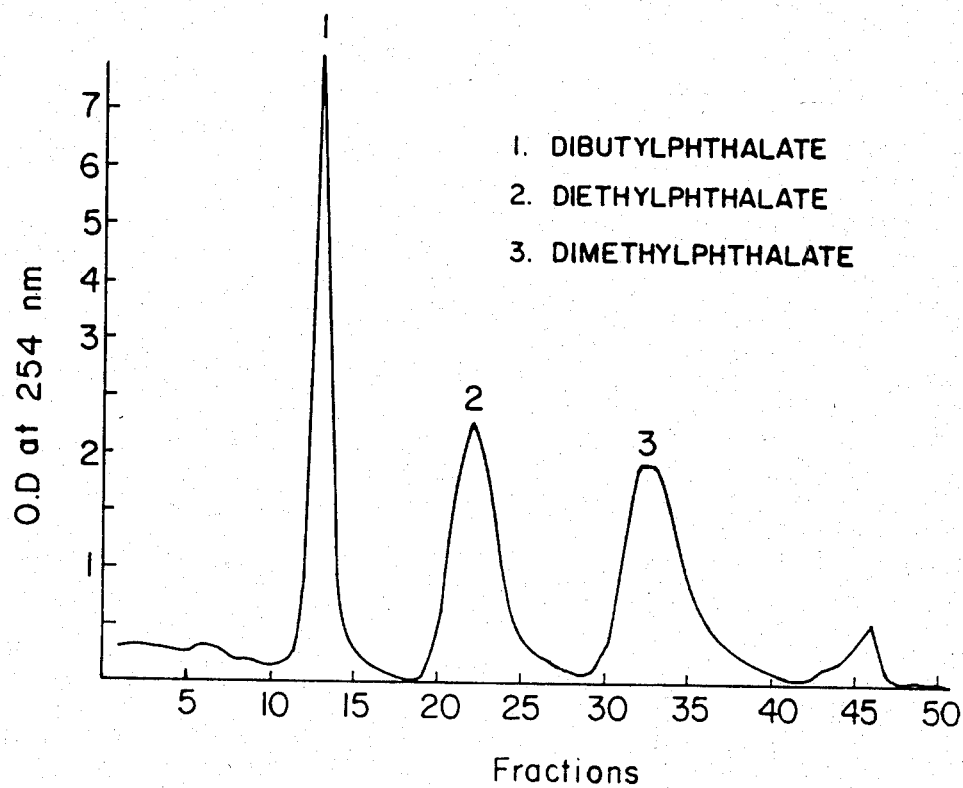

The alkyl phthalates consisted of a mixture of dibutylphthalate, diethylphthalate and dimethylphthalate in n-heptane/ethyl acetate (90/10 parts by volume). The eluant was a mixture of n-heptane/ethyl acetate (90/10 parts by volumes). The flow rate was 3 ml/min, the volume of each fraction being 1 ml. The results of the separation are presented in FIG. 12 in the form of graphs, optical density (O.D.) at 254 nm versus the fractions. As appears from the graphs a clear separation was obtained.

EXAMPLE 7

Purification of anti-hCG

The purification of anti-hCG was performed with the DCLC method using two different sources of this compounds: (a) SERONO and (b) MILES, the latter being known to be less concentrated than the former.

(a) Purification of anti-hCG (SERONO).

One vial of anti-hCG was reconstituted with 1 ml of phosphate buffer (pH=6.3). The solution was applied on a column (10.6 cm length and 10 mm internal diameter) containing 3 grams of cellulose (DEAE DE-52, Trade Mark produced by Whatman) as adsorbent. The column was eluted with phosphate buffer (pH=6.3) at a flow rate of 2.5 ml/min. Immediately a very high peak of proteins was visible in the first fractions (4 to 8). The column was connected to a flow-cell and recorder for immediate detection. A change of buffer to pH=7.1 brought an almost immediate appearance of proteins. Two other major peaks of proteins were eluted.

The determination was performed by reading on absorbance at 280 optical density (O.D.) nm each fraction. The immunological activity of each fraction of hCG recognition was done by RIA method using the following solutions: 100 μl $^{125}$I-hCG; 100 μl serum free of hCG and 100 μl of each fraction. The incubation was for 3 hours at room temperature. The separation was done using a polyethylene glycol/double antibody (20/1 volume parts).

The results obtained are presented in the following Table 5.

TABLE 5

Separation of anti-hCG SERONO on DEAE DE-52.

| Fraction No. | O.D. | RIA % binding | Fraction No. | O.D. | RIA % bind |
|---|---|---|---|---|---|
| 1 | 0.004 | 0.1% | 16 | 0.013 | 19% |
| 2 | 0.002 | 0.1% | 17 | 0.039 | 16.4% |
| 3 | 0.004 | 14.1% | 18 | 0.03 | 5.0% |
| 4 | 0.006 | 2.1% | 19 | 0.012 | 3.0% |
| 5 | 0.63 | 22.8% | 20 | 0.019 | 6.4% |
| 6 | 0.879 | 12.3% | 21 | 0.044 | 10.3% |
| 7 | 0.097 | 2.8% | 22 | 0.029 | 4.5% |
| 8 | 0.01 | 0.1% | 23 | 0.018 | 4.0% |
| 9 | 0.008 | 0.1% | 24 | 0.015 | 3.0% |
| 10 | 0.003 | 0.1% | 25 | 0.008 | 2.6% |
| 11 | — | 0.1% | 26 | 0.002 | 2.4% |
| 12 | 0.002 | 0.1% | 27 | 0.002 | 0.1% |
| 13 | 0.002 | 0.1% | 28 | 0.01 | 0.1% |
| 14 | 0.003 | 0.1% | 29 | — | 0.1% |
| 15 | 0.01 | 0.1% | | | |

As appears from the results presented in Table 5, three major peaks were obtained, the immunological activity remained extremly high in comparison to the protein concentration.

(b) Purification of anti-hCG (MILES).

70 μl of antibody (as rabbit serum) were applied to the DEAE DE-52 column, as in the previous case) and eluted first with phosphate buffer (pH=6.3). Again as in the previous case, a fast protein peak was eluted in fractions 3 and 4; by a decrease in the optical density (O.D.) and change of buffer to pH=7.1, three other major peaks were collected.

The results are presented in the following Table 6.

TABLE 6

Separation of anti-hCG MILES on DEAE-52.

| Fraction No. | O.D. | RIA % binding | Protein A* % binding | Fr. No. | O.D. | RIA % binding | Protein A* % binding |
|---|---|---|---|---|---|---|---|
| 1 | 0.01 | 0.1% | — | 21 | 0.094 | 63.6% | 7.0% |
| 2 | 0.102 | 0.1% | — | 22 | 0.042 | 64.8% | 7.2% |
| 3 | 0.656 | 64.2% | 2.6% | 23 | 0.041 | 63.4% | — |
| 4 | 0.416 | 45.6% | — | 24 | 0.07 | 1.0% | — |
| 5 | 0.091 | 0.1% | — | 25 | 0.518 | 60.3% | 5.9% |
| 6 | 0.055 | 0.1% | — | 26 | 0.518 | 67.7% | 5.3% |
| 7 | 0.044 | 0.1% | — | 27 | 0.299 | 55.5% | 4.5% |
| 8 | 0.022 | 0.1% | — | 28 | 0.161 | 58.4% | 3.7% |
| 9 | 0.016 | 0.1% | — | 29 | 0.120 | 66.0% | 2.5% |
| 10 | 0.007 | 0.1% | — | 30 | 0.112 | 54% | 1.8% |
| 11 | 0.005 | 0.1% | — | 31 | 0.091 | 51.3% | 3.9% |
| 12 | 0.003 | 0.1% | — | 32 | 0.074 | 59.7% | 2.4% |
| 13 | 0.003 | 0.1% | — | 33 | 0.062 | 55.7% | unknown |
| 14 | 0.004 | 0.1% | — | 34 | 0.062 | 60.9% | — |
| 15 | 0.001 | 0.1% | — | 35 | 0.043 | 59.5% | 1.9% |
| 16 | 0.004 | 0.1% | — | 36 | 0.034 | | |
| 17 | 0.011 | 0.1% | — | 37 | 0.035 | | |
| 18 | 0.034 | 65.4% | 7.2% | 38 | 0.029 | | |
| 19 | 0.291 | 55.5% | 12.1% | 39 | 0.021 | | |
| 20 | 0.247 | 61.4% | 11.6% | | | | |

As appears from the results presented in Table 6, the separated anti-hCG was collected in three main peaks. All of them showed immunological activity, absorption at 280 nm and recognition by Protein A*. All peaks were sharply separated from each other and collected.

EXAMPLE 8

Separation of Human Serum

A separation of human serum was executed using the DCLC method, identical to the procedure as described in Handbook of Experimental Immunology (D. M. Weir, Md. Blackwell Scientific Publications, Oxford, London, 1973 2nd ed.). The chromatography is based on ion-exchange on a cellulose adsorbent and a gradient elution with phosphate buffer (0.02M) of pH 5.7.

The column of 10 mm internal diameter was packed with 3 g of DEAE DE-52 (Trade Mark produced by Whatman) and washed with the phosphate buffer (pH=8), at flow rate of 2.5 ml/min. The gradient was produced with a two chamber system, using 40 ml phosphate buffer pH 8 and 60 ml of phosphate buffer pH 5.7. An amount of 3 ml of human serum was separated; fractions of 1.5 ml each being collected and the protein content therein was determined by optical density (O.D.) at 280 nm. The results are presented in the following Table 7.

TABLE 7

Separation of human serum (O.D. at 280 nm).

| Fr. No. | O.D. |
|---|---|
| 1 | 0.0017 |
| 2 | 1.3 |
| 3 | 1.3 |
| 4 | 1.3 |

TABLE 7-continued

Separation of human serum (O.D. at 280 nm).

| Fr. No. | O.D. |
|---|---|
| 5 | 0.554 |
| 6 | 0.262 |
| 7 | 0.135 |
| 8 | 0.082 |
| 9 | 0.067 |
| 10 | 0.064 |
| 11 | 0.055 |
| 12 | 0.052 |
| 13 | 0.052 |
| 14 | 0.061 |
| 15 | 0.102 |
| 16 | |
| 17 | 0.187 |
| 18 | 0.355 |
| 19 | 0.379 |
| 20 | 0.361 |
| 21 | 0.313 |
| 22 | 0.233 |
| 23 | 0.156 |
| 24 | 0.098 |
| 25 | 0.06 |
| 26 | 0.026 |
| 27 | 0.008 |
| 28 | 0.004 |
| 29 | 0.011 |
| 30 | 0.003 |
| 31 | 0.008 |
| 32 | 0.015 |
| 33 | 0.016 |
| 34 | 0.011 |
| 35 | 0.005 |
| 36 | 0.006 |

As appears from the results presented in Table 7, the separation achieved by DCLC shows the traditional picture of separated human serum with two major peaks (IgG, Albumins). The separation is completed in a short time.

EXAMPLE 9

In this Example the DCLC method was applied to affinity chromatography, for isolation of rabbit IgG using as ligand SEPHAROSE-4B (Trade Mark, produced by Pharmacia)-antibody (antibody=Goat-anti rabbit).

| | |
|---|---|
| SEPHAROSE-4B - antibody: | The antibody was coupled to the SEPHAROSE-4B (Trade Mark, produced by Pharmacia) adsorbent using the instructions given by Axel Porath et al (Nature 214, 1967).<br>1 g SEPHAROSE-4B ⎫<br>30 mg Goat-anti rabbit ⎭ 50% binding |
| DCLC column: | glass column of 6 mm internal diameter, packed with Sepharose-4B - antibody. |
| Detection: | was done directly from the column with flow cell. With UV at 280 nm adsorption. |
| Buffer: | 1. Phosphate buffer/NaCl, pH 7.8.<br>2. Glycine/HCl (0.1 M), pH 2.5. |

The procedure comprised the following steps:
1. Coupling of SEPHAROSE-4B to Goat-anti rabbit serum.
2. Packing of DCLC with SEPHAROSE-4B-antibody 3 ml gel, closed from both sides with a filter system VYON (Trade Mark) approx. 40 μm.
3. Washing of the packed column with 6 ml of buffer 1.
4. Loading the column with 0.5 ml N.R.S (Normal Rabbit Serum).
5. Incubation of 2 h at 37° C.

6. Elution with buffer 1 and collection of fraction until the optical density at the Photometer is below 0.1.

7. Elution with buffer 2 of pH 2.5 and collection of fractions until the optical density is below 0.1.

Figure 13:
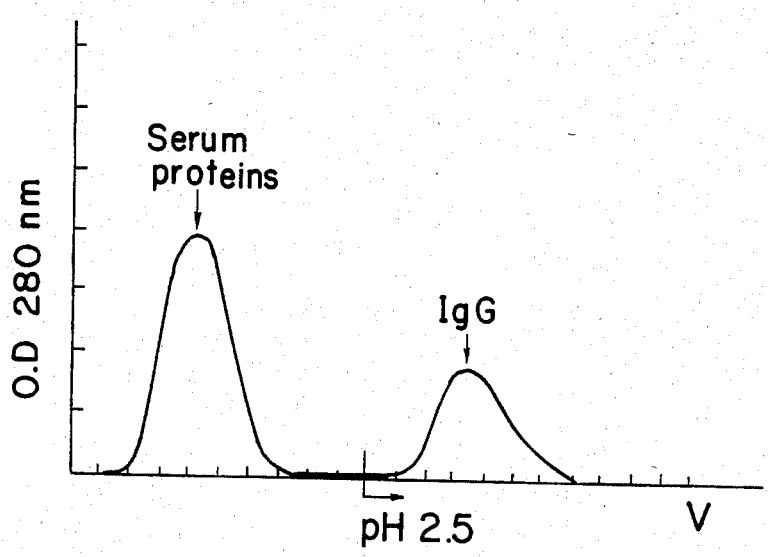
FIG. 13 represents a schematic graph for affinity chromatography of IgG isolation as described in Example 9.

A schematic graph for the affinity chromatograph of this example is presented in FIG. 13.

We claim:

1. A method for separating separable components contained in a liquid sample, comprising the steps of
   (a) adsorbing said separable components of said sample onto a movable chromatographic column comprising at least one dense-packed adsorbent bed, said column having an inlet end and on outlet end;
   (b) placing said inlet end of said column into a container defining an elongated passage adapted to accept said column in a formfitting manner, said passage containing a predetermined amount of an eluant; and
   (c) moving said column in said passage through said eluant, whereby said eluant is forced under an intrinsic pressure developed in said passage through said adsorbent bed to elute at least one of said separable components from said column at said outlet end.

2. A method according to claim 1, wherein said column comprises a plurality of serially connected adsorbent beds.

3. A method according to claim 1, wherein said adsorbent bed is comprised of at least a first adsorbent material and a second adsorbent material which is different from said first adsorbent material, said first and second adsorbent materials being separate from each other in said adsorbent bed.

4. A method according to claim 1, wherein said eluant is introduced into said passage prior to step (b).

5. A method according to claim 1, wherein said adsorbent bed is comprised of dense-packed silica gel particles.

6. A method according to claim 1, wherein said eluant is more polar than said adsorbent bed.

7. A method according to claim 1, wherein column comprises a capillary-like channel in which said adsorbent bed is disposed.

8. A method according to claim 1, wherein said column comprises an adsorbent gel bed, said method further comprising before step (a) the step of equilibrating said gel bed with a solution having a predetermined ionic concentration.

9. A method according to claim 1, wherein said adsorbent bed is composed of an ion exchanger.

10. A method according to claim 9, wherein said adsorbent bed comprises a liquid anion-exchanger and a support material impregnated with said liquid anion-exchanger.

11. A device for separating separable components contained in a liquid sample, comprising
    (1) a movable chromatographic column comprising at least one dense-packed adsorbent bed, said column having an inlet end and an outlet end;
    (2) a container defining an elongated passage adapted to accept said column;
    (3) sealing means for sealing one end of said passage; and
    (4) moving means, adapted to fit said passage in a formfitting manner, for moving said column through said passage so as to develop an intrinsic pressure in said passage.

12. A device according to claim 11, wherein said moving means comprises a piston which is adapted to fit snugly into said passage, said piston comprising at least one longitudinal channel wherein said adsorbent bed is disposed.

13. A device according to claim 12, wherein said moving means further comprises a sealing element provided on the outer surface of said piston such that said sealing element slideably contacts said passage when said piston is inserted into said passage.

14. A device according to claim 12, wherein said sealing element is comprised of an inert material.

15. A device according to claim 14, wherein said sealing element comprises a rubber O-ring disposed in an orifice bore provided in said piston.

16. A device according to claim 12, wherein said piston comprises a plurality of separate, serially connected longitudinal channels, an adsorbent bed being disposed in each channel of said plurality of longitudinal channels.

17. A device according to claim 12, wherein a first barrier and a second barrier are provided, respectively, at each end of said adsorbent column in said longitudinal channel.

18. A device according to claim 17, wherein each of said first and second barriers comprises at least one of a semipermeable membrane and a filter element.

19. A device according to claim 12, wherein said piston further comprises a conduit located at said outlet end of said column, said conduit being connected to said longitudinal channel.

20. A device according to claim 12, wherein said piston further comprises a stopper provided at one end of said piston.

21. A device according to claim 20, wherein said conduit passes through said stopper.

22. A device according to claim 11, further comprising a reservoir adapted to contain a liquid, said reservoir being connected to said container.

23. A device according to claim 12, wherein said piston further comprises entrapping means for entrapping a predetermined volume of gas in a gas pocket.

24. A device according to claim 23, wherein said entrapping means comprises at least one groove on said piston, said groove being selected from the group consisting of a horizontal groove, a vertical groove, and a spiral groove.

25. A device according to claim 11, wherein said sealing means comprises a valve.

26. A device according to claim 11, wherein said column further comprises a cartridge in which said adsorbent bed is disposed, said cartridge being formfittingly adapted to said passage.

* * * * *